United States Patent
Dahlgren et al.

(10) Patent No.: US 11,998,716 B2
(45) Date of Patent: Jun. 4, 2024

(54) VALVE ASSEMBLY

(71) Applicant: ACIST Medical Systems, Inc., Eden Prairie, MN (US)

(72) Inventors: Aron David Dahlgren, Edina, MN (US); Caleb D. Tkach, Minneapolis, MN (US); Spencer Fodness-Bondhus, Columbia Heights, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 564 days.

(21) Appl. No.: 17/160,700

(22) Filed: Jan. 28, 2021

(65) Prior Publication Data

US 2021/0236796 A1      Aug. 5, 2021

Related U.S. Application Data

(60) Provisional application No. 62/967,662, filed on Jan. 30, 2020.

(51) Int. Cl.
*A61M 39/24*         (2006.01)

(52) U.S. Cl.
CPC ..... *A61M 39/24* (2013.01); *A61M 2039/2473* (2013.01)

(58) Field of Classification Search
CPC .......... A61M 2039/229; A61M 39/223; A61M 5/1408; A61M 5/14216
See application file for complete search history.

(56) References Cited

U.S. PATENT DOCUMENTS

| 972,878 | A | * | 10/1910 | Leon ................ | A01N 1/00 27/24.1 |
|---|---|---|---|---|---|
| 1,298,680 | A | | 4/1919 | Dunham | |
| 1,496,126 | A | | 6/1924 | Livingstone | |

(Continued)

FOREIGN PATENT DOCUMENTS

| CA | 2312632 A1 | 12/2001 |
|---|---|---|
| CN | 2187955 | 1/1995 |

(Continued)

OTHER PUBLICATIONS

"Oldham's Coupling," Oct. 18, 2013, XP002804706, retrieved from the Internet: URL:https://blogpuneet.wordpress.com/2013/10/08/oldhams-coupling/comment-page-1/[retrieved on Nov. 4, 2021], 2 pgs.

(Continued)

*Primary Examiner* — Courtney B Fredrickson
(74) *Attorney, Agent, or Firm* — Crowell & Moring LLP

(57) ABSTRACT

A valve assembly embodiment includes first and second valve devices and a coupling mechanism. Each of the first and second valve devices can include first and second fluid pathways and first and second valve members respectively positioned at the first and second fluid pathways. Both the first and second valve members can have an open position that permits fluid flow and a closed position that prevents fluid flow along the first and second fluid pathways past the first and second valve members. The coupling mechanism can couple to each of the first and second valve members. When the valve assembly is actuated, the coupling mechanism can be configured to transition one or both of the first and second valve members between the open and closed positions.

20 Claims, 12 Drawing Sheets

(56) References Cited

U.S. PATENT DOCUMENTS

| | | |
|---|---|---|
| 1,937,122 A | 11/1933 | Leach |
| 2,538,662 A | 1/1951 | Abbott |
| 2,893,390 A | 7/1959 | La et al. |
| 2,985,182 A | 5/1961 | Williams |
| 3,299,904 A | 1/1967 | Burke |
| 3,359,910 A | 12/1967 | Latham, Jr. |
| 3,405,545 A | 10/1968 | Walker |
| 3,411,534 A | 11/1968 | Rose |
| 3,802,463 A | 4/1974 | Dabney |
| 3,808,895 A | 5/1974 | Fitzwater |
| 3,813,077 A | 5/1974 | Kolic |
| 3,861,421 A | 1/1975 | Thompson |
| 3,918,490 A | 11/1975 | Goda |
| 3,941,128 A | 3/1976 | Baldwin |
| 4,061,142 A | 12/1977 | Tuttle |
| 4,096,070 A | 6/1978 | Servas |
| 4,282,902 A | 8/1981 | Haynes |
| 4,286,442 A | 9/1981 | Peterson |
| 4,332,148 A | 6/1982 | Maki et al. |
| 4,396,385 A | 8/1983 | Kelly et al. |
| 4,452,592 A | 6/1984 | Tsai |
| 4,484,599 A | 11/1984 | Hanover et al. |
| 4,585,442 A | 4/1986 | Mannes |
| 4,645,489 A | 2/1987 | Krumme et al. |
| 4,969,486 A | 11/1990 | Puzio |
| 5,071,329 A | 12/1991 | Sano et al. |
| 5,113,906 A | 5/1992 | Hoegner |
| 5,117,870 A | 6/1992 | Goodale et al. |
| 5,399,172 A | 3/1995 | Martin et al. |
| 5,421,780 A | 6/1995 | Vukovic |
| 5,439,452 A | 8/1995 | Mccarty |
| 5,458,581 A | 10/1995 | Hull |
| 5,533,708 A | 7/1996 | Atkinson et al. |
| 5,542,832 A | 8/1996 | Sone et al. |
| 5,573,515 A | 11/1996 | Wilson et al. |
| 5,583,630 A | 12/1996 | Kimura et al. |
| 5,611,458 A | 3/1997 | Ogden et al. |
| 5,704,773 A | 1/1998 | Higashiyama |
| 5,769,385 A | 6/1998 | Burrous et al. |
| 5,797,889 A | 8/1998 | Steinman |
| 5,851,201 A | 12/1998 | Ritger et al. |
| 5,901,745 A | 5/1999 | Buchtel |
| 6,017,332 A | 1/2000 | Urrutia |
| 6,221,045 B1 | 4/2001 | Duchon et al. |
| 6,517,439 B1 | 2/2003 | Sears |
| 6,565,535 B2 | 5/2003 | Zaias et al. |
| 6,656,157 B1 | 12/2003 | Duchon et al. |
| 7,617,837 B2 | 11/2009 | Wilson et al. |
| 7,985,140 B2 | 7/2011 | Maki et al. |
| 8,152,780 B2 | 4/2012 | Evans et al. |
| 8,851,172 B1 | 10/2014 | Dudzinski |
| 9,739,289 B2 | 8/2017 | Oda et al. |
| 2003/0084943 A1 | 5/2003 | Tischler et al. |
| 2005/0255426 A1 | 11/2005 | Mariaulle et al. |
| 2007/0161970 A1 | 7/2007 | Spohn et al. |
| 2008/0058720 A1 | 3/2008 | Spohn et al. |
| 2008/0103446 A1 | 5/2008 | Torrance et al. |
| 2009/0149743 A1 | 6/2009 | Barron et al. |
| 2010/0130958 A1 | 5/2010 | Kang et al. |
| 2010/0280462 A1 | 11/2010 | Kommireddy et al. |
| 2012/0065502 A1 | 3/2012 | Levy et al. |
| 2013/0053692 A1 | 2/2013 | Barron et al. |
| 2013/0066202 A1 | 3/2013 | Barron et al. |
| 2013/0067416 A1 | 3/2013 | Barron et al. |
| 2013/0261599 A1* | 10/2013 | Haueter ............ A61M 5/16809 604/152 |
| 2014/0107480 A1 | 4/2014 | Spohn et al. |
| 2016/0166742 A1* | 6/2016 | Layser .................... A61M 1/72 604/32 |
| 2016/0202708 A1 | 7/2016 | Hurst |
| 2017/0281922 A1* | 10/2017 | Baid ..................... A61M 39/22 |
| 2017/0370493 A1 | 12/2017 | Sigg et al. |
| 2018/0344142 A1 | 12/2018 | Abouzgheib |
| 2020/0033897 A1 | 1/2020 | Jensen et al. |

FOREIGN PATENT DOCUMENTS

| | | |
|---|---|---|
| CN | 2244409 | 1/1997 |
| CN | 201046277 Y | 4/2008 |
| CN | 101244299 A | 8/2008 |
| CN | 101355975 A | 1/2009 |
| CN | 101461972 A | 6/2009 |
| EP | 1055432 | 11/2000 |
| EP | 1410815 A1 | 4/2004 |
| GB | 2274326 A | 7/1994 |
| JP | 8602369 A | 1/1985 |
| JP | H0796033 A | 4/1995 |
| WO | 0024313 A1 | 5/2000 |
| WO | 0155626 | 8/2001 |
| WO | 2005110007 A2 | 11/2005 |
| WO | 2007062315 A2 | 5/2007 |
| WO | 2011002744 A1 | 1/2011 |
| WO | 2011073969 A1 | 6/2011 |

OTHER PUBLICATIONS

PCT International Search Report and Written Opinion dated May 31, 2021 for related International Application No. PCT/US2021/015396, 13 pgs.

"Surface Roughness," chart of amplitude parameters, Retrieved from the Internet <URL:https://en.wikipedia.org/wiki/Surface_roughness> on Sep. 18, 2017, 8 pages.

Wikipedia page—https://en.wikipedia.org/wiki/Coupling (see Section 2.1.21: Oldham), "Wikipedia Coupling, Oldham Coupler," retrieved from the Internet on Oct. 10, 2020, believed to be available prior to the filing date of the instant application (Aug. 21, 2020), 2 pages.

Simulation on YouTube: https://www.youtube.com/watch?v=2ibsOu_TrZc, Oldham Coupling, May 29, 2015, 71 pages.

Off the shelf Oldham couplings: https://www.ruland.com/servo-couplings/oldham-couplings.html, "Ruland Oldham Coupling," retrieved from the Internet on Oct. 23, 2020, believed to be available prior to the filing date of the instant application (Aug. 21, 2020), 8 pages.

\* cited by examiner

SECT. A-A

```
                    ┌─────────────────────────────────────┐
                    │ Actuate valve assembly to move first │
                    │ valve member from open to closed     │
                    │ position and second valve member     │
                    │ from closed to open position         │
              1005  └─────────────────────────────────────┘
                                      │
                                      ▼
                    ┌─────────────────────────────────────┐
                    │ Actuate valve assembly to maintain   │
                    │ first valve member in closed position│
                    │ and move second valve member from    │
                    │ open to closed position              │
              1010  └─────────────────────────────────────┘
                                      │
                                      ▼
                    ┌─────────────────────────────────────┐
                    │ Actuate valve assembly to move first │
                    │ valve member from closed to open     │
                    │ position and maintain second valve   │
                    │ member in closed position            │
              1015  └─────────────────────────────────────┘
```

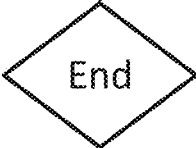

FIG. 9

VALVE ASSEMBLY

RELATED APPLICATIONS

The present application claims priority to Provisional Patent Application No. 62/967,662 filed Jan. 30, 2020, the entire contents of which is incorporated herein by reference.

TECHNICAL FIELD

This disclosure generally relates to valve assemblies, systems, and methods. Certain valve assembly, system, and method embodiments are described herein in the exemplary context of fluid flow in a medical application, such as a medical fluid injection.

BACKGROUND

Valves can be used to control fluid flow in a variety of contexts, including in the medical context. For example, certain medical procedures may include introducing a fluid into a patient. Various medical devices can be employed to introduce fluid into a patient. In conjunction with a particular procedure, such medical devices may selectively start and stop injecting fluid into a patient by opening or closing a fluid pathway leading to the patient. Depending on the particular procedure, a medical device may need to introduce multiple fluids into a patient. This may call for selective opening and closing of multiple fluid pathways in various coordinated sequences in order to achieve desired flow states at the medical device throughout the duration of a particular procedure.

SUMMARY

Embodiments disclosed herein can provide coordinated transitioning of valve members between opened and closed positions and, thereby, facilitate various flow states as needed at different times during a fluid injection procedure. This can help medical devices, such as fluid injectors, carry out a fluid injection procedure that implements multiple fluid flow states throughout the procedure. The ability to coordinate open and closed position transitions amongst multiple valve members can be useful in reducing user error, and thereby increasing safety and convenience of the injection procedure.

Disclosed herein are exemplary embodiments of valve assemblies, systems, and methods as well as fluid injection system embodiments incorporating such valve assembly, system, and method embodiments. For instance, certain such embodiments can be configured to fluidly connect to a fluid reservoir of a fluid injection system such that fluid flow both into and out of the fluid reservoir can be controlled in a coordinated manner. This can include, for example, coordinated transitioning of two or more valves between open and closed positions to achieve each of multiple flow states at the fluid injection system at appropriate times throughout a fluid injection procedure. Some such embodiments can be configured to require only a single input (e.g., movement of a component coupled to each of the two or more valve members) to coordinate control of two or more valves in transitioning a fluid injection system from one flow state to another, different flow state. As one such example, two or more valves can be controlled in a coordinated manner to transition a fluid injection system from a fill operational flow state to an inject operational flow state.

One exemplary embodiment includes a valve assembly. This valve assembly embodiment includes a first valve device, a second valve device, and a coupling mechanism. The first valve device can include a first fluid pathway and a first valve member. The first valve member can be positioned at the first fluid pathway. The first valve member can have a first valve member open position that permits fluid flow along the first fluid pathway past the first valve member and a first valve member closed position that prevents fluid flow along the first fluid pathway past the first valve member. The second valve device can include a second fluid pathway and a second valve member. The second valve member can be positioned at the second fluid pathway. The second valve member can have a second valve member open position that permits fluid flow along the second fluid pathway past the second valve member and a second valve member closed position that prevents fluid flow along the second fluid pathway past the second valve member. The coupling mechanism can be coupled to each of the first valve member and the second valve member. When the valve assembly is actuated, the coupling mechanism can be configured to move each of the first valve member from the first valve member open position to the first valve member closed position and the second valve member from the second valve member closed position to the second valve member open position.

In a further embodiment of the valve assembly, when the valve assembly is further actuated, the coupling mechanism can be further configured to move the second valve member from the second valve member open position to the second valve member closed position. For example, when the valve assembly is further actuated to move the second valve member from the second valve member open position to the second valve member closed position, the coupling mechanism can be further configured to maintain the first valve member at the first valve member closed position. In one such embodiment, the first valve member closed position can include a first valve member first closed position and a first valve member second closed position that is different from the first valve member first closed position. In such embodiment, the coupling mechanism can be configured to maintain the first valve member at the first valve member closed position by moving the first valve member from the first valve member first closed position to the first valve member second closed position.

In a further embodiment of the valve assembly, when the valve assembly is further actuated, the coupling mechanism can be further configured to move the second valve member from the second valve member open position to the second valve member closed position. When the valve assembly is further actuated, the coupling mechanism can be further configured to move the second valve member from the second valve member open position to the second valve member closed position. For example, when the second valve member is in the second valve member closed position and the valve assembly is further actuated, the coupling mechanism can be further configured to move the first valve member from the first valve member closed position to the first valve member open position. In one such example, when the valve assembly is further actuated to move the first valve member from the first valve member closed position to the first valve member open position, the coupling mechanism can be further configured to maintain the second valve member at the second valve member closed position. The second valve member closed position can include a second valve member first closed position and a second valve member second closed position that is different from the second valve member first closed position. The coupling mechanism can be configured to maintain the second valve member at the second valve member closed position, for instance, by moving the second valve member from the second valve member first closed position to the second valve member second closed position.

In a further embodiment of the valve assembly, when the valve assembly is actuated, the coupling mechanism can be configured to move, at the same time, each of the first valve member from the first valve member open position to the first valve member closed position and the second valve member from the second valve member closed position to the second valve member open position.

Another exemplary embodiment includes a fluid injection system. This fluid injection system embodiment can include a reservoir, a drive assembly, and a valve assembly. The valve assembly can be the same as, or similar to, that of the first discussed embodiment. The reservoir can define an interior reservoir volume. The reservoir can include a plunger positioned within the interior reservoir volume. The drive assembly can be configured to move the plunger within the interior reservoir volume to draw an injection fluid into the reservoir and to expel the injection fluid from the reservoir. The valve assembly can be fluidly connected to the reservoir. When the valve assembly is actuated, the coupling mechanism can be configured to move each of the first valve member from the first valve member open position to the first valve member closed position and the second valve member from the second valve member closed position to the second valve member open position.

A further exemplary embodiment includes a method of regulating fluid flow in a fluid injection system. In a step of this method, the valve assembly can be actuated to move each of the first valve member from the first valve member open position to the first valve member closed position and the second valve member from the second valve member closed position to the second valve member open position. In another step of this method, the valve assembly can be actuated to maintain the first valve member in the first valve member closed position and move the second valve member from the second valve member open position to the second valve member closed position. In a further step of this method, the valve assembly can be actuated to move the first valve member from the first valve member closed position to the first valve member open position and the second valve member from the second valve member closed position to the second valve member open position.

The details of one or more examples are set forth in the accompanying drawings and the description below. Other features, objects, and advantages will be apparent from the description and drawings.

BRIEF DESCRIPTION OF DRAWINGS

The following drawings are illustrative of particular embodiments of the present invention and therefore do not limit the scope of the invention. The drawings are intended for use in conjunction with the explanations in the following description and are not necessarily to scale. Embodiments of the invention will hereinafter be described in conjunction with the appended drawings, wherein like numerals denote like elements.

FIG. 1 shows the fluid injection system including an embodiment of a valve assembly.

FIG. 3A is a perspective view of the valve assembly of FIG. 1. FIG. 3B is a side elevational view of the valve assembly of FIG. 1. FIG. 3C is a cross sectional view of the valve assembly taken along line A-A in FIG. 3A. And, FIG. 3D is a close up of details B and C shown in FIG. 3C. Detail B shows a first valve member and detail C shows a second valve member.

FIG. 4A shows the first valve member in a first valve member open position and the second valve member in a second valve member closed position. FIG. 4B shows the first valve member in a first valve member closed position and the second valve member in a second valve member open position. FIG. 4C shows the first valve member in a first valve member second closed position and the second valve member in a second valve member second closed position.

FIG. 7A is a perspective view of this coupling mechanism embodiment. FIG. 7B is another perspective view of this coupling mechanism embodiment rotated 90 degrees, about its longitudinal axis, relative to the view shown in FIG. 7A.

FIG. 9 is a flowchart showing an embodiment of a method of regulating fluid flow in a fluid injection system.

DETAILED DESCRIPTION

Figure 1:
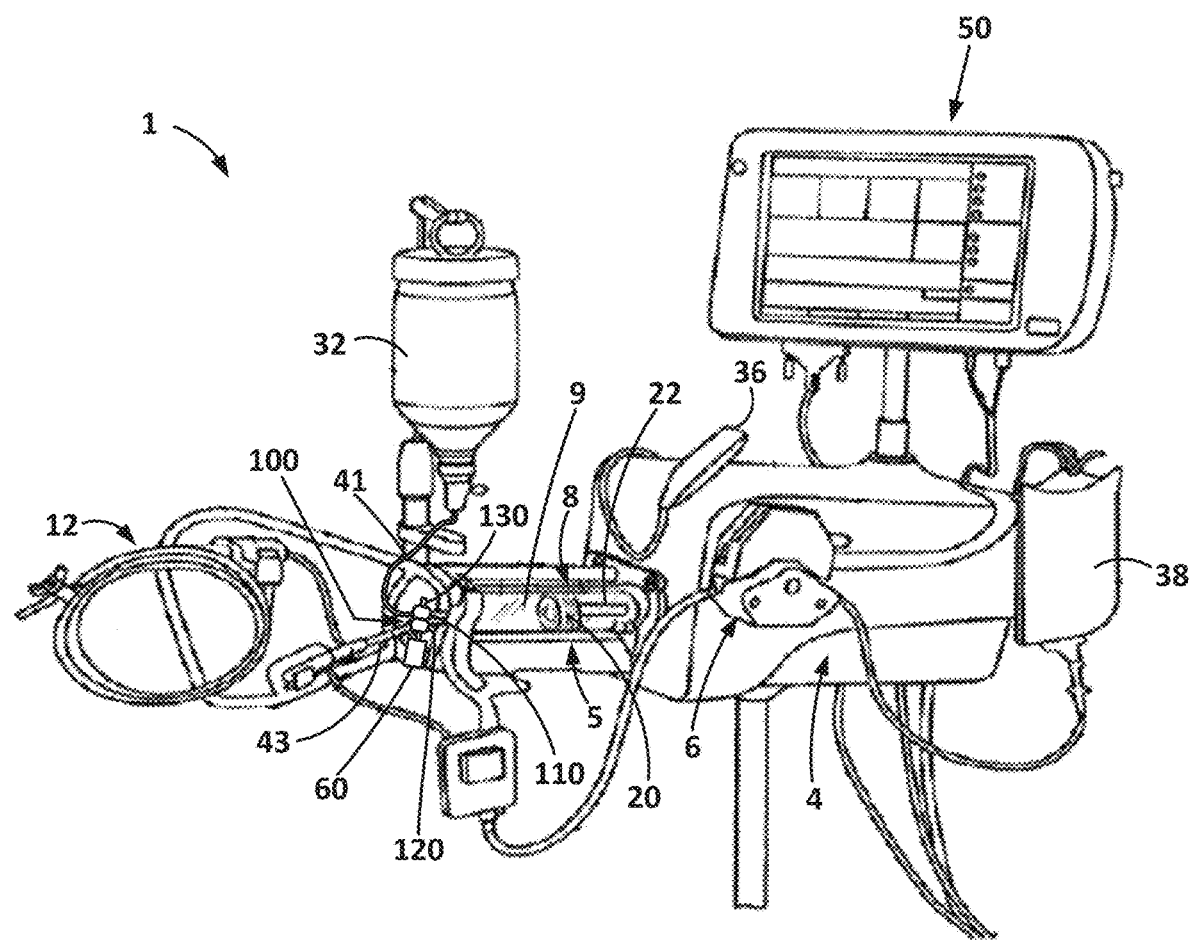
FIG. 1 is perspective view of an embodiment of a fluid injection system.

The following detailed description is exemplary in nature and provides some practical illustrations and examples. Those skilled in the art will recognize that many of the noted examples have a variety of suitable alternatives. A number of various exemplary systems, assemblies, and methods are disclosed herein using the description provided as follows in addition to the accompanying drawings. Each of the systems, assemblies, and methods disclosed herein can be employed independently or in combination with one or more (e.g., all) of the other systems, assemblies, and methods disclosed herein. Like reference numerals are used in this description, and in the drawings, to convey like elements.

FIG. 1 shows a perspective view of an illustrative embodiment of a fluid injection system 1. The fluid injection system 1, as shown in FIG. 1, includes an embodiment of a valve assembly 100 at or near, shown here fluidly connected to, a reservoir 8 of the fluid injection system 1.

The fluid injection system 1 can be used in certain medical procedures to inject one or more fluids into a patient. In such procedures, as further described below, it can be useful to draw injection fluid into the reservoir 8 of the fluid injection system 1, purge the reservoir 8 of air, and pressurize and expel injection fluid from the reservoir 8 such that the pressurized fluid is introduced into the patient.

In the illustrated example, the fluid injection system 1 is a powered fluid injection system 1. The powered fluid injection system 1 can be used to inject a quantity of one or more fluids into a patient's vessel (e.g., via a catheter assembly at the patient). The fluid injected by the powered fluid injection system 1 can be, for example, a contrast fluid, non-contrast fluid (e.g., saline), or a combination of contrast and non-contrast fluid. Exemplary medical procedures performed in connection with the powered fluid injection system 1 can include OCT imaging, IVUS imaging, angiographic procedures, and other forms of diagnostic imaging procedures. The powered fluid injection system 1 can include the reservoir 8, a drive assembly, and a valve assembly 100, each of which can be used during operation of the powered fluid injection system 1. The reservoir 8 can be secured at the powered fluid injection system 1 by a sleeve 5. One or both of the valve assembly 100 and drive assembly, which can be at an injector head 4, can be coupled to the reservoir 8.

Fluid to be introduced into a patient using the powered fluid injection system 1 can be held and pressurized in the reservoir 8. The reservoir 8 can define an interior reservoir volume 9, which can hold the injection fluid. The reservoir 8 can include a plunger 20 positioned within the interior reservoir volume 9. The reservoir 8 can include a reservoir inlet and a reservoir outlet (shown, e.g., in FIG. 2). In the illustrated embodiment, the reservoir inlet and the reservoir outlet are positioned opposite the drive assembly that is at the injector head 4. The plunger 20 is coupled to a drive shaft 22 of the drive assembly. The drive assembly can include the drive shaft 22 and a motor component, housed within the injector head 4, coupled to the drive shaft 22. The drive assembly can be configured to move the drive shaft 22, and thus plunger 20, forward and rearward within the reservoir 8.

To both fill the reservoir 8 with fluid and expel fluid from the reservoir 8, the plunger 20 can be moved within the reservoir 8 toward or away from the reservoir outlet as a result of the drive assembly moving the drive shaft 22. Both the drive assembly and, via the drive shaft 22, the plunger 20 can receive an operative force from a motor housed within the injector head 4. The operative force from this motor can cause movement of the drive shaft 22, which can thereby move the plunger 20 forward or rearward within the reservoir 8. Moving the plunger 20 forward within the reservoir 8 can move the plunger 20 toward the reservoir outlet. This forward movement of the plunger 20 can pressurize fluid within the reservoir 8 and expel this fluid from the reservoir 8 through the reservoir outlet. Moving the plunger 20 rearward within the reservoir 8 can move the plunger 20 away from the reservoir outlet. This rearward movement of the plunger 20 can create a vacuum within the reservoir 8 and thereby drawn fluid into the reservoir 8, through the reservoir inlet, to fill the reservoir 8 with fluid. Thus, the drive assembly can be configured to move the plunger 20 within the interior reservoir volume 9 to draw the injection fluid into the reservoir 8 (e.g., via the reservoir inlet) and to pressurize and expel the injection fluid from the reservoir 8 (e.g., via the reservoir outlet).

The powered fluid injection system 1 can include one or more fluid containers with a supply of fluid to be injected into the patient during a procedure. For example, fluid in a first container 32, such as contrast fluid, can be drawn into the reservoir 8 by moving, via the drive assembly, the plunger 20 rearward within the reservoir 8 during operation of the powered fluid injection system 1. In some cases, filling the reservoir 8 with the contrast fluid introduces an amount of air into the reservoir 8, which, to ensure a safe injection, is purged from the reservoir 8 before the contrast fluid is injected into the patient. Thus, after fluid is drawn into the reservoir 8, the reservoir 8 can be purged of air by moving the plunger 20 forward a first distance. The contrast fluid within the reservoir 8 can be further pressurized (e.g., up to 1,300 psi) by moving the plunger 20 forward a further, second distance and delivered to the patient (e.g., an injection) by continuing to move the plunger 20 forward within the reservoir 8. As another example, fluid in a second container 38, such as a non-contrast fluid (e.g., a flushing fluid, such as saline), can be delivered to the patient by the pump 6 (e.g., a peristaltic pump delivering non-contrast fluid via displacement). Each of the contrast fluid and the non-contrast fluid can be conveyed along patient tubing 12 and introduced into the patient via a catheter at the patient.

A user, e.g., an operator, of the powered fluid injection system 1 can control and monitor the operation of the powered fluid injection system 1 via one or more of its components. In some embodiments, the powered fluid injection system 1 can include a hand-control device 36 to help control certain operational aspects of the powered fluid injection system 1. A user can manipulate the hand-control device 36 to control injection of fluid from the powered fluid injection system 1. For example, a user can use the hand-control device 36 to start and stop a fluid injection. In some cases, a user can use a control panel 50 of the powered fluid injection system 1 to set up or modify various parameters and/or injection protocols for a given fluid injection procedure. For instance, the user can interact with the control panel 50 to input injection protocols such as flow rate, injection volume, injection duration and/or other injection parameters. The control panel 50 can be controlled by one or more processors, which may also control other components of the powered fluid injection system 1. Multiple injection operations of the powered fluid injection system 1 can be controlled and implemented during a given patient procedure and over a number of patient procedures.

Because the powered fluid injection system 1 may perform multiple operations, e.g., injections, over a number of patient procedures, injection fluids may need to be continuously replenished. The injector head 4 may automatically replenish fluid to the reservoir 8, for example, based upon monitoring of injection volumes therefrom and comparing to an initial, input, volume; or the operator of the powered fluid injection system 1 may need to manually initiate a fluid replenishment procedure, upon detection that a fluid volume within the reservoir 8 has been depleted to a threshold volume. It should be noted that the injector head 4 may automatically replenish fluid to the reservoir 8 based upon operational state information, other than injection volumes. For example, if the injector head 4 determines that the powered fluid injection system 1 is currently delivering fluid from the pump 6, but not from the reservoir 8, and that the reservoir 8 is not filled to capacity, the injector head 4 may cause the motor assembly to move the plunger 20, via the drive assembly, to draw additional fluid into the reservoir 8, via the fill tubing 41.

Delivering and refilling injection fluid may require different flow states (e.g., combinations of open and closed states of each valve device) of the powered fluid injection system 1 to achieve the desired operation. For instance, when filling the reservoir 8 it can be desirable between the reservoir inlet and the contrast fluid container 32 to have a valve device, of the valve assembly 100, open and between the reservoir outlet and the patient to have a valve device, of the valve assembly 100, closed. On the other hand, when injecting a fluid from the reservoir 8 it can be desirable between the reservoir inlet and the contrast fluid container 32 to have a valve device, of the valve assembly 100, closed and between the reservoir outlet and the patient to have a valve device, of the valve assembly 100, open. And, when the reservoir is not being filled and no fluid is being injected, it can be desirable to close both the valve device between the reservoir inlet and the contrast fluid container 32 and the valve device between the reservoir outlet and the patient.

Because different operations of the fluid injector can require different flow states, it can be desirable to control such flow states according to the operation to be performed. For instance, often times a single injection procedure for a patient can require multiple flow states, including reservoir fill and inject flow states. The valve assembly 100 can be used to facilitate and transition between the various flow states. For instance, as shown in FIG. 1, both the fill tubing 41 and the injection tubing 43 can include actuatable valve device to allow or impede fluid past the corresponding valve. Transitioning between certain flow states may require actuating both of these valve devices. Notably, the valve assembly 100 can use one output (e.g., from the powered fluid injection system 1) to transition both of the valve devices amongst the various flow states needed to carry out various injection procedures.

In the illustrated embodiment of the powered fluid injection system 1, the valve assembly 100 can be used to regulate fluid flow at the powered fluid injection system 1 by controlling first and second valve devices 110, 120 of the valve assembly 100. The valve assembly 100 can be fluidly connected to the reservoir 8 and include the first valve device 110 with a first valve member positioned at a first fluid pathway, a second valve device 120 with a second valve member positioned at a second fluid pathway. The valve assembly 100 can also include a coupling mechanism 130 coupled to each of the first and second valve devices 110, 120. The valve assembly 100, when actuated, can be configured to move each of the first valve member and the second valve member between open and closed positions. Such actuations, in some examples, may only require a single input and/or movement of a single component of the valve assembly 100. In this way, the valve assembly 100 can readily regulate fluid flow through the reservoir 8 of the powered fluid injection system 1 by transitioning both of the valve devices amongst the various flow states (e.g., via the coupling mechanism 130) to achieve the various certain flow states needed to facilitate the particular injection operations (e.g., fill, inject, etc.).

As shown in FIG. 1, the valve assembly 100 can be fluidly connected to the reservoir 8. When fluidly connected to the reservoir 8, each of the first valve device 110 and the second valve device 120 can control fluid flow into and out of the reservoir 8. The coupling mechanism 130 can be coupled to each of the first valve member, of the first valve device 110, and the second valve member, of the second valve device 120. When the valve assembly 100 is actuated, the coupling mechanism 130 can be configured to transition one or both of the first valve member and the second valve member between an open and closed position. For instance, as one example, when the valve assembly 100 is actuated, the coupling mechanism 130 can move each of the first valve member from a first valve member open position to a first valve member closed position and the second valve member from a second valve member closed position to a second valve member open position. As another example, when the valve assembly 100 is actuated, the coupling mechanism 130 can move one of the first valve member and second valve member from one of an open position and a closed position to the other of the open position and a closed position and maintain the other of the first valve member and the second valve member is its open or closed position.

In the illustrated embodiment, the powered fluid injection system 1 includes a motive source 60 configured to provide a motive force to actuate the valve assembly 100. The motive source 60 can be coupled to the coupling mechanism 130. Although illustrated here as being outside of the injector head 4, other examples of the powered fluid injection system 1 may include the motive source 60 at other portions of the powered fluid injection system 1, including at (e.g., within) the injector head 4. As one example, the motive source 60 can be a motor driven by the powered fluid injection system 1 (e.g., driven by the injector head 4). In such example, the motor can be controlled by a controller of the powered fluid injection system (e.g., the control panel 50). The controller can control the motive force that the motor provides to the valve assembly 100, such as via the coupling mechanism 130, to thereby control the position (e.g., open, closed) of the valve members of the valve devices 110, 120. In this way, the controller can implement one or more changes to the positions of the valve members of the valve assembly 100 and thereby control the flow states present at the valve assembly 100.

The coupling mechanism 130 includes an actuation portion having an actuation attachment, which connects to the motive source 60 and receives the motive force to actuate the valve assembly 100. As discussed further below, in some cases, to couple to the motive source 60, the actuation attachment can include a key that is complementarily received by a motive source 60 component corresponding to the key. As the motive source 60 moves (e.g., continuously or intermittently rotates, pivots, turns, etc.), the motive force is received by the key thereby correspondingly moving the coupling mechanism 130. Such movement of the coupling mechanism 130 can move both the first valve member and the second valve member between respective open and closed positions. Certain operations of the powered fluid injection system 1 may require the first and second valve members to be in the same or different positions.

The powered fluid injection system 1 can be configured to perform a fill operation to draw the injection fluid into the reservoir 8 through a reservoir inlet and to perform an injection operation to expel the injection fluid from the reservoir 8 through a reservoir outlet. For example, the first valve device 110 can be coupled to the reservoir inlet and the second valve device 120 can be coupled to the reservoir outlet. Depending on the operation, the flow state of the powered fluid injection system 1 may change. For example, when the powered fluid injection system 1 performs the fill operation, the plunger 20 can be moved within the reservoir 8 away from the reservoir outlet by the drive assembly while the first valve member is in the first valve member open position and the second valve member is in the second valve member closed position. When the powered fluid injection system 1 performs the inject operation, the plunger 20 can be moved within the reservoir 8 toward the reservoir outlet by the drive assembly while the first valve member is in the first valve member closed position and the second valve member is in the second valve member open position. And when the powered fluid injection system 1 is not performing the fill operation or the injection operation, both the first valve member and the second valve member can be in their respective closed positions. For a given operation in a procedure, actuating a valve assembly 100 that is coupled to the reservoir 8 can facilitate the powered fluid injection system 1 moving between these flow states.

Figure 2:
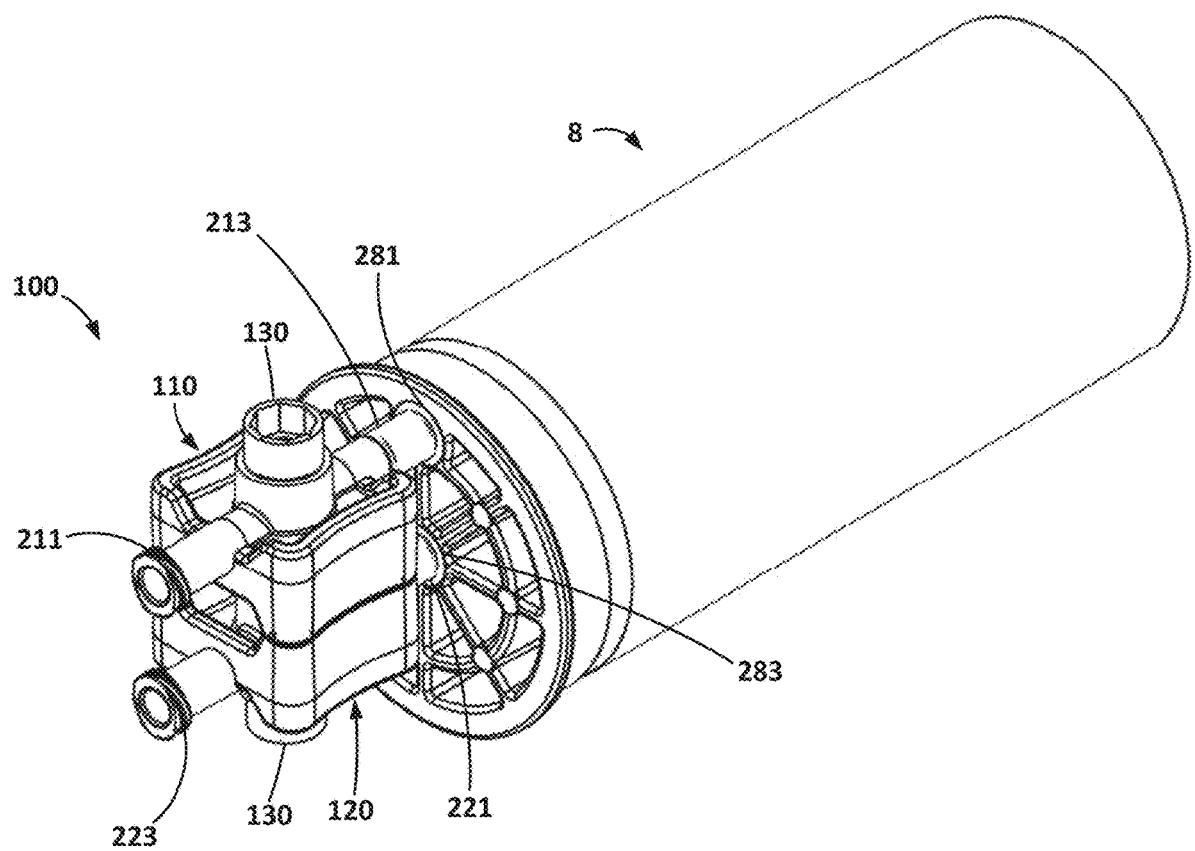
FIG. 2 is a perspective view of the valve assembly and the reservoir of FIG. 1.

FIG. 2 shows a perspective view of the valve assembly 100 and the reservoir 8. As noted, the valve assembly 100, including both the first valve device 110 and the second valve device 120, can be fluidly connected to the reservoir 8. The first valve device 110 can include a first fluid inlet 211 and a first fluid outlet 213, and the second valve device 120 can include a second fluid inlet 221 and a second fluid outlet 223. The reservoir 8 can include a reservoir inlet 281 and a reservoir outlet 283. In the illustrated example, the first fluid outlet 213 is fluidly connected to (e.g., directly coupled to) the reservoir inlet 281, and the second fluid inlet 221 is fluidly connected to (e.g., directly coupled to) the reservoir outlet 283. Both the first fluid inlet 211 and the second fluid outlet 223 can be coupled to other components of the fluid injection system, for example via tubing as discussed elsewhere herein. Exemplary features of the valve assembly 100 will be discussed in more detail as follows.

Figure 3A:
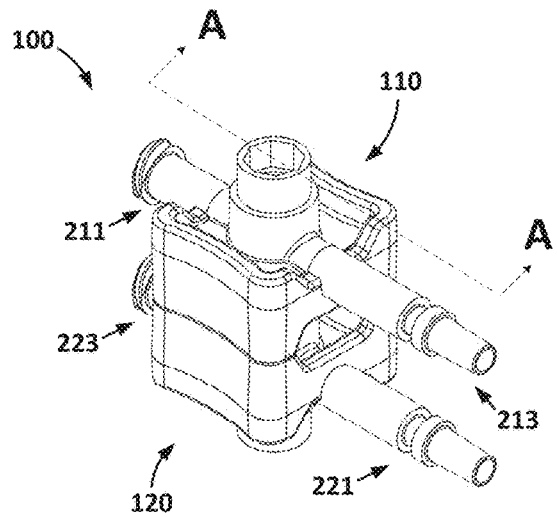
FIGS. 3A-3D show features of the valve assembly.
Figure 3B:
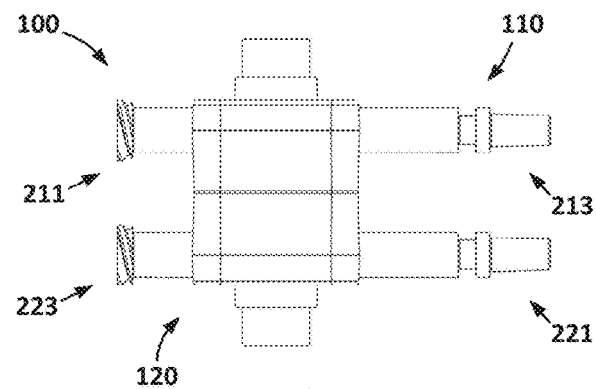
Figure 3C:
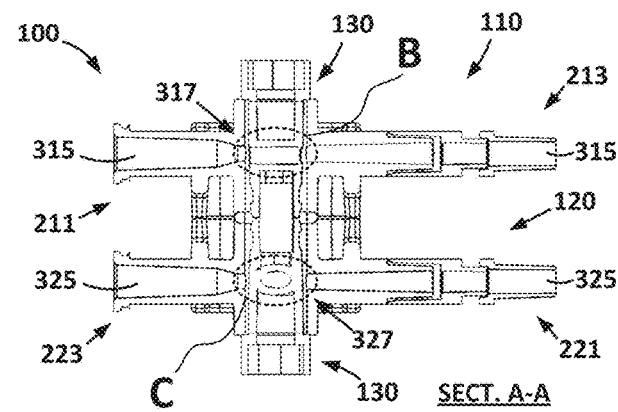
Figure 3D:
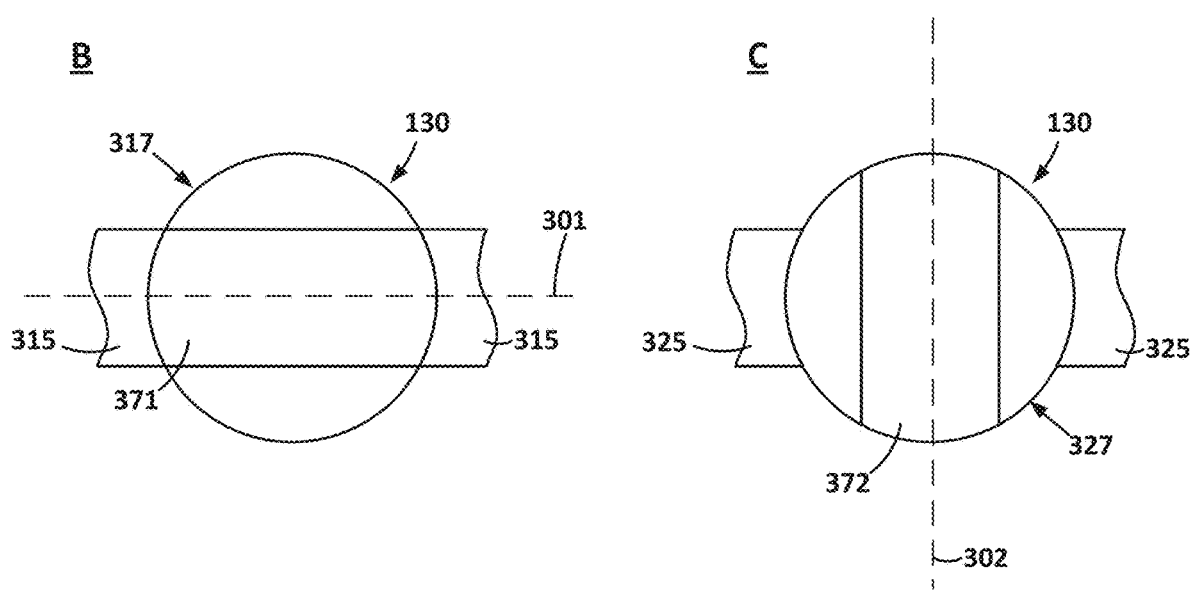

FIGS. 3A-3D show exemplary features of the valve assembly 100. FIG. 3A shows a perspective view of the valve assembly 100. FIG. 3B shows a side elevational view of the valve assembly 100. FIG. 3C shows a cross sectional view of the valve assembly 100 taken along line A-A in FIG. 3A. And, FIG. 3D shows a close up of details B and C, in FIG. 3C, with detail B showing one position of a first valve member 317 and detail C showing one position of a second valve member 327.

In the embodiment shown in FIGS. 3A-3D, the valve assembly 100 includes the first valve device 110 and the second valve device 120. As can be seen in FIGS. 3C and 3D, the first valve device 110 can include a first fluid pathway 315 and the first valve member 317. The first valve member 317 can be positioned at the first fluid pathway 315. As can also be seen in FIGS. 3C and 3D, the second valve device 120 can include a second fluid pathway 325 and the second valve member 327. The second valve member 327 can be positioned at the second fluid pathway 325. As shown, the coupling mechanism 130 can be coupled to each of the first valve member 317 and the second valve member 327. Fluid flow can be regulated by the first valve member 317 and the second valve member 327 such that fluid selectively flows through the valve assembly 100 from the first fluid inlet 211 to the first fluid outlet 213 and from the second fluid inlet 221 to the second fluid outlet 223.

Positions of the first and second valve members 317, 327, for instance as shown in FIG. 3C, can facilitate regulating fluid flow at the first and second fluid pathways 315, 325 and thus through the valve assembly 100. The first fluid pathway 315 can extend between the first fluid inlet 211 and the first fluid outlet 213. The first valve member 317 can be positioned at the first fluid pathway 315 between the first fluid inlet 211 and the first fluid outlet 213. The second fluid pathway 325 can extend between the second fluid inlet 221 and the second fluid outlet 223. The second valve member 327 can be positioned at the second fluid pathway 325 between the second fluid inlet 221 and the second fluid outlet 223. Because the first and second valve members 317, 327 are positioned as such at the first and second fluid pathways respectively, fluid flow past the first and second valve members 317, 327 can be permitted or prevented by opening and closing the first and second valve members 317, 327.

For example, preventing fluid flow can mean at least substantially impeding fluid flow. As one such example of substantially impeding fluid flow, each of the first valve member 317 and the second valve member 327 can have an allowable leakage rate that is nominal with respect to a fluid flow rate that is allowed past each of the first valve member 317 and the second valve member 327 when opened. For example, the allowed leakage rate can include an amount of fluid (e.g., less than 1 mL, less than 0.5 mL, less than 0.25 mL) during a certain procedure (e.g., an injection during which fluid is pressurized up to 1,300 psi) for a certain period of time (e.g., less than 10 seconds, such as between 3 and 7 seconds).

Actuating each of the first valve member 317 and the second valve member 327 between respective open and closed positions can regulate fluid flow at the valve assembly 100. With reference to FIG. 3D, the first valve member 317 can have a first valve member open position, such as that shown in FIG. 3D, that permits fluid flow along the first fluid pathway 315 past the first valve member 317. The first valve member 317 can be actuated to transition to a first valve member closed position that prevents fluid flow along the first fluid pathway 315 past the first valve member 317. The second valve member 327 can have a second valve member closed position, such as that shown in FIG. 3D, that prevents fluid flow along the second fluid pathway 325 past the second valve member 327. The second valve member 327 can be actuated to transition to a second valve member open position that permits fluid flow along the second fluid pathway 325 past the second valve member 327. For instance, when the valve assembly 100 is actuated, the coupling mechanism 130 can be configured to transition one or both of the first valve member 317 between the first valve member open position and the first valve member closed position and the second valve member 327 between the second valve member open position to the second valve member closed position.

FIG. 3D shows the relative position between the first fluid pathway 315 and the second fluid pathway 325. The first valve member 317 can include a first valve fluid pathway 371 extending along a first plane 301 through the first valve member 317. The first valve fluid pathway 371 can be in fluid communication with the first fluid pathway 315 when the first valve member 317 is in the first valve member open position, such as in FIG. 3D. The second valve member 327 can include a second valve fluid pathway 372 extending along a second plane 302 through the second valve member 327. The second valve fluid pathway 372 can be in fluid communication with the second fluid pathway 325 when the second valve member 327 is in the second valve member open position. In some examples, the first plane 301 can have a non-parallel position relative to the second plane 302 when one of the first and second valve members 317, 327 is in the open position and the other of the first and second valve members 317, 327 is in the closed position. For instance, the shown first fluid pathway 315 and second fluid pathway 325 are positioned such that the first plane 301 is perpendicular to the second plane 302 when one of the first and second valve members 317, 327 is in the open position and the other of the first and second valve members 317, 327 is in the closed position.

Figure 4A:
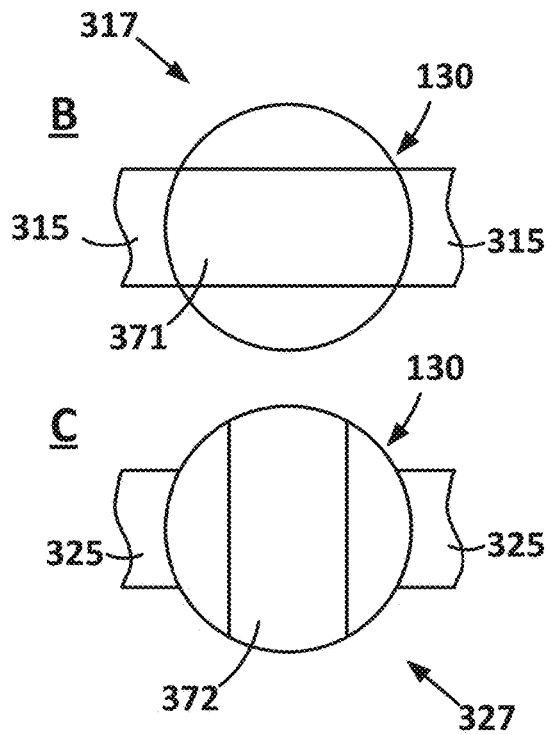
FIGS. 4A-4C show close ups of details B and C (shown in FIGS. 3C and 3D) with the first and second valve members, of the embodiment of the valve assembly, at various positions.
Figure 4B:
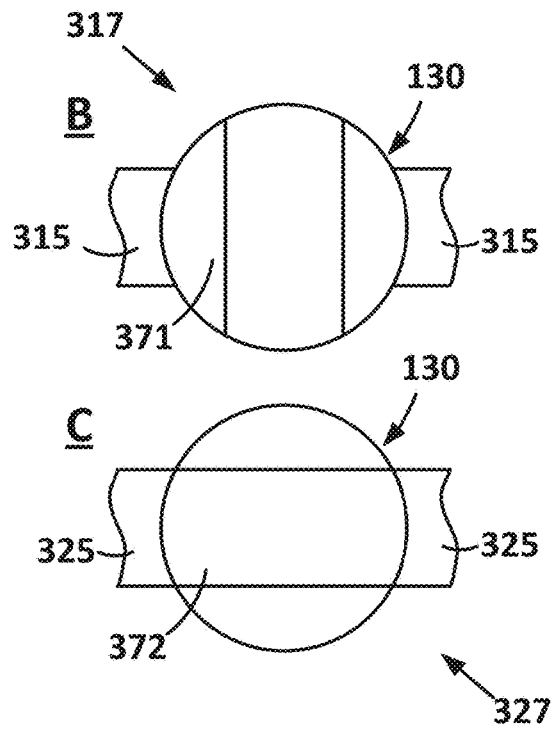
Figure 4C:
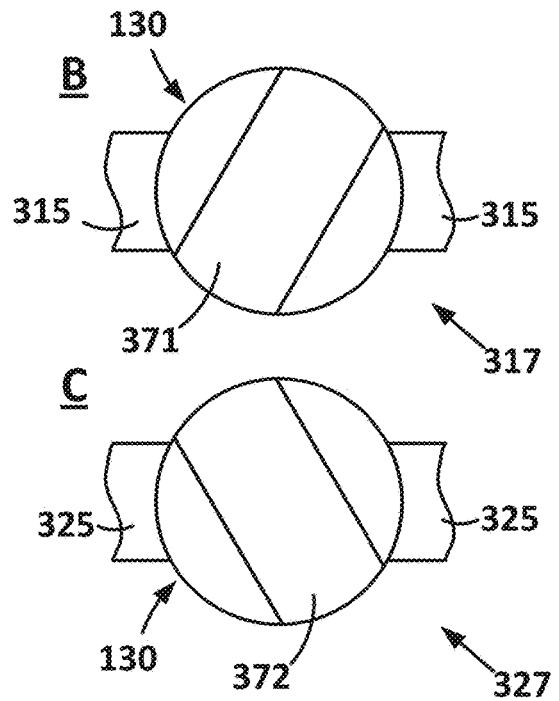

FIGS. 4A-4C show close ups of details B and C (shown in FIGS. 3C and 3D) with the first and second valve members 317, 327 at various positions. FIG. 4A shows the first valve member 317 in a first valve member open position and the second valve member 327 in a second valve member closed position. FIG. 4B shows the first valve member 317 in a first valve member closed position and the second valve member 327 in a second valve member open position. FIG. 4C shows the first valve 317 member in a first valve member second closed position and the second valve member 327 in a second valve member second closed position. In FIGS. 4A-4C, detail B shows a position of the first valve member 317 and detail C shows a position of the second valve member 327.

FIG. 4A shows an initial flow state where the first valve member 317 is in the first valve member open position and the second valve member 327 is in the second valve member closed position. This initial flow state, with the first valve member 317 is in the first valve member open position and the second valve member 327 is in the second valve member closed position, could used, for example, in a reservoir fluid fill operation and/or a reservoir purge operation. FIG. 4B shows a subsequent flow state after the valve assembly has been actuated from the flow state shown in FIG. 4A. In the subsequent flow state shown in FIG. 4B, the first valve member 317 is in the first valve member closed position and the second valve member 327 in the second valve member open position. FIG. 4C shows a further subsequent flow state after the valve assembly has been actuated from the flow state shown in FIG. 4B. In the further subsequent flow state of FIG. 4C, the first valve member 317 in the first valve member closed position and the second valve member 327 in the second valve member closed position. As described further below, and as illustrated by the closed positions of the first valve member 317 in FIGS. 4B and 4C and the closed positions of the second valve member 327 in FIGS. 4A and 4C, each of the first valve member closed position and the second valve member closed position can include more than one close position (e.g., a first and second closed position).

Other useful features of the valve assembly can be seen in FIGS. 4A-4C. In particular, each of the states shown in FIGS. 4A-4C can be achieved, for example, with less than a 180 degree rotation (e.g., clockwise) of the coupling mechanism 130 and, by extension, arrived at least twice in less than a 360 degree rotation of the coupling mechanism 130. Such features can increase the useful life of the valve assembly, such as by minimizing the amount of wear on a connected motive source (and coupling mechanism 130) and the valve member components by reducing the amount of movement needed to transition the valve members between positions defining various flow states.

During operation, the valve assembly may undergo one or more actuations (e.g., a first, second, third, and fourth actuation), which can transition one or both of the first and second valve members 317, 327 between open and closed positions. For example, when the valve assembly is actuated the coupling mechanism can be configured to move each of the first valve member from the first valve member open position, for instance as shown in FIG. 4A, to the first valve member closed position, for instance as shown in FIG. 4B, and the second valve member from the second valve member closed position, for instance as shown in FIG. 4A, to the second valve member open position, for instance as shown in FIG. 4B (e.g., the first actuation).

When the valve assembly is further actuated, the coupling mechanism 130 can be further configured to move the second valve member 327 from the second valve member open position, for instance as shown in FIG. 4B, to the second valve member closed position, for instance as shown in FIG. 4C. When the valve assembly is further actuated to move the second valve member 327 from the second valve member open position to the second valve member closed position, the coupling mechanism 130 can be further configured to maintain the first valve member 317 at the first valve member closed position (e.g., the second actuation), for instance by moving the first valve member 317 from the first valve member first closed position shown in FIG. 4B to the first valve member second closed position shown in FIG. 4C.

When the second valve member 327 is in the second valve member closed position, for instance as shown in FIG. 4C, and the valve assembly is further actuated, the coupling mechanism 130 can be further configured to move the first valve member 317 from the first valve member closed position, for instance as shown in FIG. 4C, to the first valve member open position (e.g., the third actuation), for instance as shown in FIG. 4A. In cases where the first, second, and third actuations are sequential and accomplished by rotation of the valve members 317, 327 in a same direction at each actuation, the first valve member 317 can rotate 180 degrees to go from the first valve member open position, shown in FIG. 4A and prior to the first actuation, to the first valve member open position resulting from the third actuation. When the valve assembly 100 is further actuated to move the first valve member 317 from the first valve member closed position to the first valve member open position, the coupling mechanism 130 can be further configured to maintain the second valve member 327 at the second valve member closed position (e.g., the fourth actuation), for instance by moving the second valve member 327 from the second valve member closed position shown in FIG. 4C to a second valve member closed position rotated 45 degrees clockwise from that shown in FIG. 4C. In some cases, the first, second, third, and fourth actuations occur sequentially, and in other cases, the first, second, third, and fourth actuation can occur in a nonsequential manner.

As described in the above examples, maintaining a closed position can include moving a valve member between different closed positions. For example, each of first valve member closed position and second valve member closed position can be accomplished when the respective valve member is at more than one rotational position. For instance, the first valve member closed position can include a first valve member first closed position and a first valve member second closed position that is different from the first valve member first closed position. And the second valve member closed position can include a second valve member first closed position and a second valve member second closed position that is different from the second valve member first closed position. In some cases, the coupling mechanism 130 can be configured to maintain the first valve member 317 at the first valve member closed position by moving the first valve member 317 from the first valve member first closed position to the first valve member second closed position (e.g., moving the first valve member 317 from the first closed position shown in FIG. 4B to the second closed position shown in FIG. 4C). And the coupling mechanism 130 can be configured to maintain the second valve member 327 at the second valve member closed position by moving the second valve member 327 from the second valve member first closed position to the second valve member second closed position (e.g., moving the second valve member 327 from the first closed position shown in FIG. 4C to the second closed position rotated 90 degrees clockwise from that shown in FIG. 4C). In some examples, the first and second valve members 317, 327 can include additional closed positions, including a third closed position achieved by rotating the coupling mechanism 130 clockwise by 45 degrees from the position shown in FIG. 4A.

Actuating each of the first valve member 317 and the second valve member 327 can be performed simultaneously in some embodiments. For example, the coupling mechanism 130 can be configured to move the first valve member 317 and the second valve member 327 between their respective open and closed positions, such as those shown in FIGS. 4A-4C, at the same time. When the valve assembly is actuated, the coupling mechanism 130 can be configured to move, at the same time, each of the first valve member 317 from the first valve member open position to the first valve member closed position and the second valve member 327 from the second valve member closed position to the second valve member open position.

In one embodiment, the valve first and second valve members 317, 327 can be actuated to turn in more than one direction. For example, as shown in the illustrated example of FIGS. 4A-4C, both of the first and second valve members 317, 327 are rotated in a clockwise direction between the valve member open and closed positions. Specifically, in this illustrated example, the first valve member 317 is actuated to turn clockwise from the first valve member open position in FIG. 4A to the first valve member closed position in FIG. 4B and the second valve member 327 is actuated to turn clockwise from the second valve member closed position in FIG. 4A to the second valve member open position shown in FIG. 4B. Likewise in this illustrated example, the first valve member 317 is actuated to turn clockwise from the first valve member closed position in FIG. 4B to the first valve member closed position in FIG. 4C and the second valve member 327 is actuated to turn clockwise from the second valve member open position in FIG. 4B to the second valve member closed position shown in FIG. 4C.

In another example, both of the first and second valve members 317, 327 can be actuated to rotate in a counterclockwise direction between the valve member open and closed positions. Specifically, in such an example, the first valve member 317 is actuated to turn counterclockwise from the first valve member open position in FIG. 4A to the first valve member closed position in FIG. 4B and the second valve member 327 is actuated to turn counterclockwise from the second valve member closed position in FIG. 4A to the second valve member open position shown in FIG. 4B. Likewise in this example, the first valve member 317 is actuated to turn counterclockwise from the first valve member closed position in FIG. 4B to the first valve member closed position, which would be the inverse of that shown in FIG. 4C, and the second valve member 327 is actuated to turn counterclockwise from the second valve member open position in FIG. 4B to the second valve member closed position, which would be the inverse of that shown in FIG. 4C.

In a further example, one or both of the first and second valve members 317, 327 can be actuated to rotate both clockwise and counterclockwise. For example, depending on the flow state desired at the first and/or second valve member 317, 327, the first and/or second valve member 317, 327 can be actuated to rotate clockwise to achieve one flow state (e.g., open position) and rotated counterclockwise to achieve another flow state (e.g., closed position).

Figure 5:
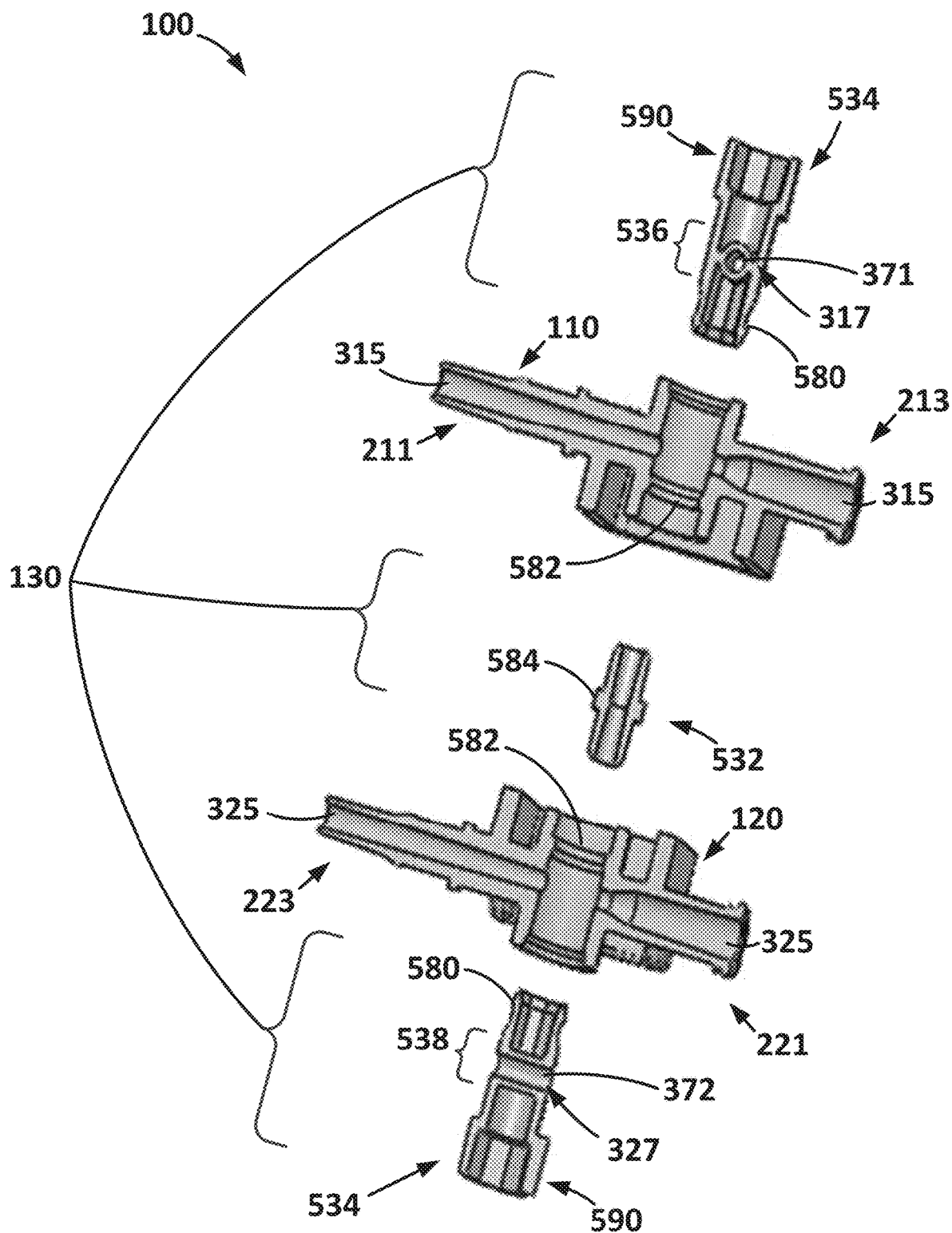
FIG. 5 is an exploded, perspective view of a cross section of the valve assembly taken along line A-A in FIG. 3A.
Figure 6:
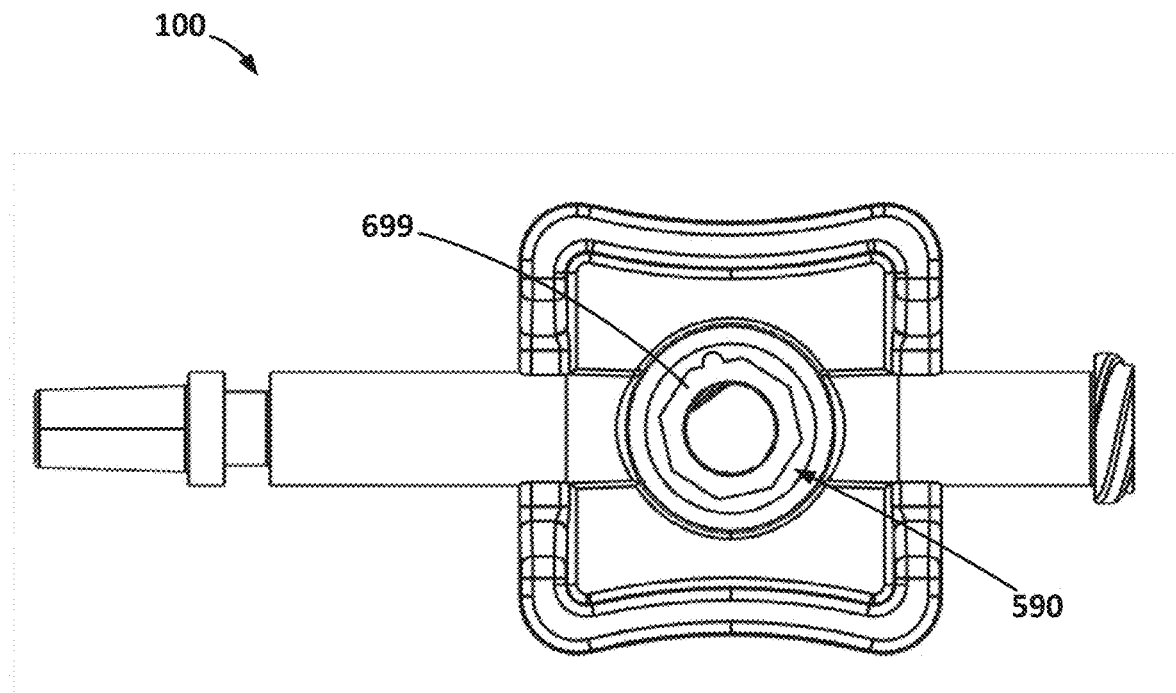
FIG. 6 is a plan view of the embodiment of the valve assembly with the coupling mechanism including a key.

4A shows an initial flow state where the first valve member 317 is in the first valve member open position and the second valve member 327 is in the second valve member closed position. This initial flow state, with the first valve member 317 is in the first valve member open position and the second valve member 327 is in the second valve member closed position, could be used, for example, in a reservoir fluid fill operation and/or a reservoir purge operation. FIG. 4B shows a subsequent flow state after the valve assembly has been actuated from the flow state shown in FIG. 4A. In the subsequent flow state shown in FIG. 4B, the first valve member 317 is in the first valve member closed position and the second valve member 327 in the second valve member open position. FIG. 4C shows a further subsequent flow state after the valve assembly has been actuated from the flow state shown in FIG. 4B. In the further subsequent flow state of FIG. 4C, the first valve member 317 in the first valve member closed position and the second valve member 327 in the second valve member closed position FIGS. 5-6 illustrate exemplary features of the valve assembly 100, including features of the first and second valve devices 110, 120 and the coupling mechanism 130. FIG. 5 shows an exploded, perspective view of a cross section of the valve assembly 100 taken along line A-A in FIG. 3A. FIG. 6 shows a plan view of the valve assembly 100 where the coupling mechanism 130 includes a key 699.

The arrangement of inlets and outlets in the valve assembly 100, as shown in FIG. 5, can facilitate coupling the valve assembly 100 to the reservoir in a fluid injection system. The first fluid inlet 211 can be opposite the first fluid outlet 213, and the second fluid inlet 221 can be opposite the second fluid outlet 223. The first fluid pathway 315 can be parallel to the second fluid pathway 325. The first fluid inlet 211 can be adjacent to the second fluid outlet 223, and the first fluid outlet 213 can be adjacent to the second fluid inlet 221. For instance, in the valve assembly embodiment shown here the first fluid inlet 211 can be aligned with the second fluid outlet 223 and the first fluid outlet 213 can be aligned with the second fluid inlet 221. As shown in the example here, the first fluid inlet 211 and the second fluid inlet 221 are on opposite sides of the valve assembly 100 and the first fluid outlet 213 and the second fluid outlet 223 are on opposite side of the valve assembly 100. In some examples, this arrangement of the first fluid outlet 213 and second fluid inlet 221 coincides with the arrangement of mating components of the reservoir (e.g., at the reservoir inlet and reservoir outlet, respectively). As such, both the first fluid outlet 213 and the second fluid inlet 221 can be configured to couple to the reservoir.

The coupling mechanism 130 can include a number of portions for facilitating various functions. The coupling mechanism 130 can include a coupling portion 532 and an actuation portion 534. In the illustrated embodiment, the coupling portion 532 and the actuation portion 534 can be at spaced apart locations along the coupling mechanism 130 and formed by separate components. In other embodiments, as discussed further below, the coupling portion 532 and the actuation portion 534 can be a single piece. Where the coupling mechanism 130 includes separate portions as shown in FIG. 5, the coupling portion 532 can be configured to couple to the actuation portion 534. In some such coupling mechanisms, features (e.g., an inner or outer profile or the like) of the coupling portion 532 can be configured to complimentarily mate with corresponding portions of the actuation portion 534.

As shown in FIG. 5, the coupling portion 532 can be configured to couple to each of the first valve member 317 and the second valve member 327. For example, the coupling mechanism 130 can include a first valve portion 536 forming the first valve member 317 and including the first valve fluid pathway 371. In this example, the coupling mechanism 130 can also include a second valve portion 538 forming the second valve member 327 and including the second valve fluid pathway 372.

The coupling portion 532 can have one end coupled to the first valve portion 536 and another end coupled to the second valve portion 538. To facilitate coupling between the coupling portion 532 and the valve portions 536, 538, the coupling mechanism 130 can include flanges 580. At least one of the first valve device 110 and the second valve device 120, in this case both of the first valve device 110 and the second valve device 120, can include a retainer 582 configured to receive the respective flanges 580. The coupling mechanism 130 can be directly received by each of the first valve device 110 and the second valve device 120 such that the coupling mechanism 130 is retained within the first valve device 110 and the second valve device 120 at the flange 580. The coupling between each of the flanges 580 and the retainer 582 can facilitate rotational movement of each of the valve portions 536, 538 relative to the respective first and second valve devices 110, 120. The coupling between the respective flanges 580 and retainers 582 may include a variety of connections, including snap-fit, resilient, and flange-and-protrusion connections. In some examples, other portions of the coupling mechanism 130 (e.g., the coupling portion 532 or the first and second valve portions 536, 538) can additionally or alternatively employ a similar connection to at least one of the first and second valve devices 110, 120. For example, the coupling portion 532 can include a lip 584 that can be configured to retain the coupling portion 532, and thus the coupling mechanism 130, within the first and second valve devices 110, 120 at the flange 580. Other features of the coupling mechanism 130 can facilitate coupling to other components of the fluid injection system.

In the illustrated example in FIG. 5, both opposite ends of the coupling mechanism 130 include the actuation portion 534. Each such actuation portion 534 is positioned at an end of each of the first valve portion 536 and second valve portion 538 that is opposite an end coupled to the coupling portion 532.

The example shown in FIG. 5 shows the actuation portions 534 having an actuation attachment 590 that is configured to couple to a motive source to receive a motive force to actuate the valve assembly 100. As shown in FIG. 6, the actuation attachment 590 can include a key 699 configured to be complementarily received by a motive source component corresponding to the key 699. For instance, the key 699 can be configured to be complementarily received by a slot within the motive source component. When received, the key 699 can align the coupling mechanism 130 with the motive source component. The key 699 can take a variety of geometric arrangement suitable for coupling (e.g., rotational coupling) with the motive source. For instance, the key 699 can form one of a male luer and female luer type configuration while the slot can form the other complimentary configuration of the male luer and female luer.

Certain fluid injection systems may use tubing to convey fluid to and from the valve assembly 100. In such systems, the valve assembly 100 can include a connector for this tubing (e.g., at the first fluid inlet and/or second fluid outlet).

Figure 7A:
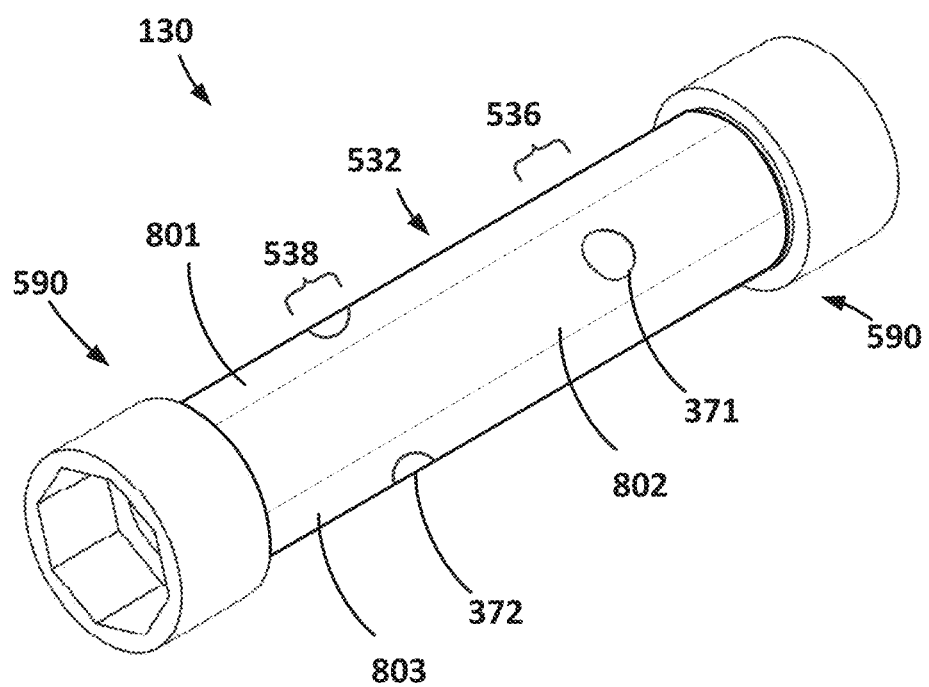
FIGS. 7A-7B show another embodiment of coupling mechanism.
Figure 7B:
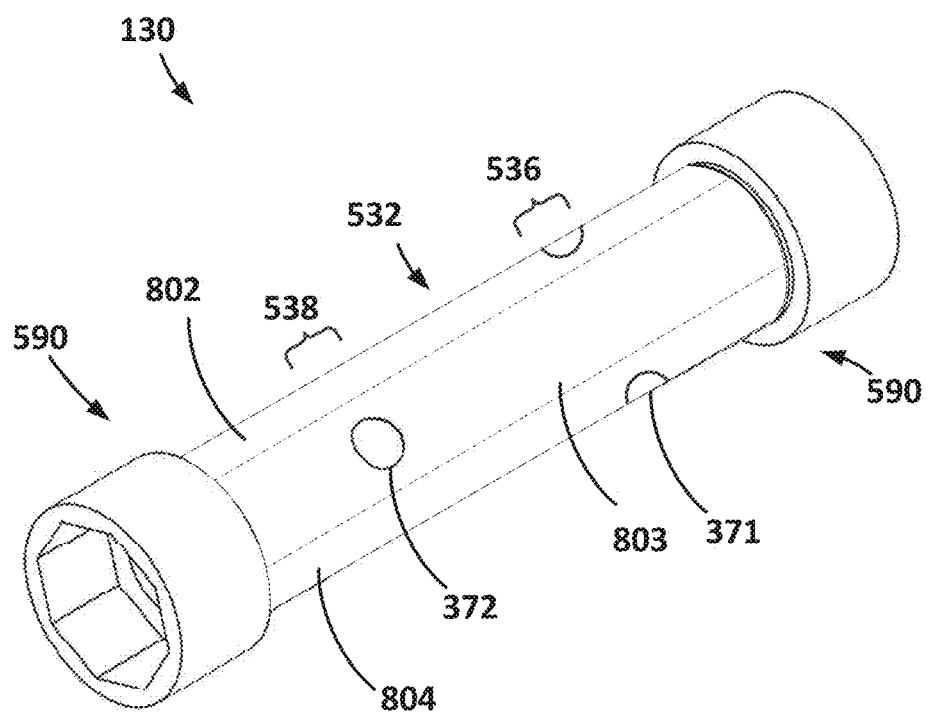
Figure 8:
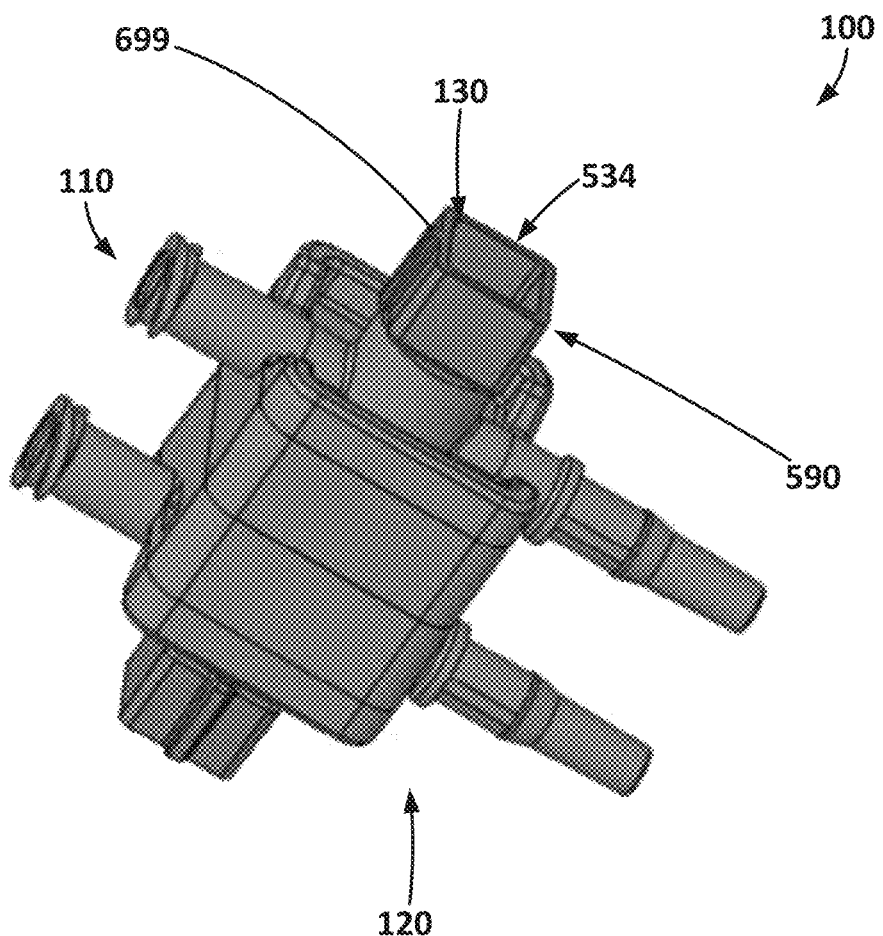
FIG. 8 is a perspective view of another embodiment of a valve assembly.

FIGS. 7A, 7B, and 8 show alternate embodiments relating to the valve assembly.

FIGS. 7A and 7B show an embodiment of the coupling mechanism 130 that is a single piece. In the embodiment shown in FIGS. 7A and 7B, each of the coupling portion 532 and the actuation portion 534 can be integrated to form a single-piece coupling mechanism 130. FIG. 7B shows this embodiment of the coupling mechanism 130 rotated 90 degrees, for that shown in FIG. 7A, to make certain sections more visible.

As shown here, the coupling mechanism 130 can include a plurality of actuation sections spaced about a periphery of the coupling mechanism 130. The plurality of actuation sections can include a first actuation section 801, a second actuation section 802, a third actuation section 803, and a fourth actuation section 804. Together, the first, second, third, and fourth actuation sections can span a perimeter surface (e.g., circumference) of the coupling mechanism 130. The first valve portion 536 can extend along a first length of the coupling mechanism 130 and can be located at a portion of each of the first actuation section 801, the second actuation section 802, the third actuation section 803, and the fourth actuation section 804. The first valve fluid pathway 371 can extend through at least two of the first actuation section 801, the second actuation section 802, the third actuation section 803, and the fourth actuation section 804. The second valve portion 538 can extend along a second length of the coupling mechanism 130 and can be located at a portion of each of the first actuation section 801, the second actuation section 802, the third actuation section 803, and the fourth actuation section 804. The first length can be different from the second length. The second valve fluid pathway 372 can extend through at least two of the first actuation section 801, the second actuation section 802, the third actuation section 803, and the fourth actuation section 804.

In the illustrated embodiment, first valve fluid pathway 371 and the second valve fluid pathway 372 each extend between two apertures, one that can serve as a fluid inlet and the other that can serve as a fluid outlet. In other embodiments, one or both of the first valve fluid pathway 371 and the second valve fluid pathway 372 can extend between more than two apertures. For instance, in such other embodiments, one or both of the first valve fluid pathway 371 and the second valve fluid pathway 372 can extend between three or more apertures (e.g., extending between three apertures such that the fluid pathway forms a "T" branch configuration). The first valve fluid pathway 371 and/or the second valve fluid pathway 372 extending between three or more apertures can be useful, for instance, in addition to the apertures proving a fluid inlet and a fluid outlet, in providing an aperture that can be used to introduce a sterilization medium (e.g., a sterilizing fluid, such as gas) into the fluid pathway.

FIG. 8 shows an alternate embodiment of a valve assembly 100 where the first valve device 110 and the second valve device 120 are integrated as a single-piece valve device. The valve devices 110, 120 can have other features similar to, or the same as, those described previously with respect to the valve devices 110, 120.

In the valve assembly embodiment shown in FIG. 8, the actuation portion 534 of the coupling mechanism 130 can have a varied geometry as compared to the previously described valve assembly embodiment. As illustrated, the actuation attachment 590 at the actuation portion 534 has a generally squared cross-sectional shape with the key 699 extending along an outer surface of at least one side of the squared cross-sectional shape. The particular shape of the actuation portion 534, and actuation attachment 590, can be such as to compliment, and couple to, the motive source.

FIG. 9 is a flowchart illustrating an embodiment of a method 1000 of regulating fluid flow in a fluid injection system. The valve assembly used in the method 1000 can have one or more (e.g., each) of the features disclosed herein. In the method 1000, the actuations of the valve assembly can be performed by the motive source in the fluid injection system. As further example, the steps of the method 1000 can be employed to perform one or both of the fill operation and the injection operation as described elsewhere herein.

At step 1005, the method 1000 includes actuating the valve assembly to move each of the first valve member from the first valve member open position to the first valve member closed position and the second valve member from the second valve member closed position to the second valve member open position. As one example, the actuation step 1005 can be performed when transitioning the valve assembly of the fluid injection system from a flow state used for filling and/or purging a reservoir to a flow state used for injecting a fluid.

At step 1010, the method 1000 include actuating the valve assembly to maintain the first valve member in the first valve member closed position and move the second valve member from the second valve member open position to the second valve member closed position. As one example, the actuation step 1010 can be performed when transitioning the valve assembly of the fluid injection system from the flow state used for injecting a fluid to a flow state used when the fluid injection system has finished an injection procedure.

At step 1015, the method 1000 incudes actuating the valve assembly to move the first valve member from the first valve member closed position to the first valve member open position and maintain the second valve member in the second valve member closed position. As one example, the actuation step 1015 can be performed when transitioning the valve assembly of the fluid injection system from the flow state used when the fluid injection system has finished an injection procedure to the flow state used for filling and/or purging a reservoir.

Figure 10:
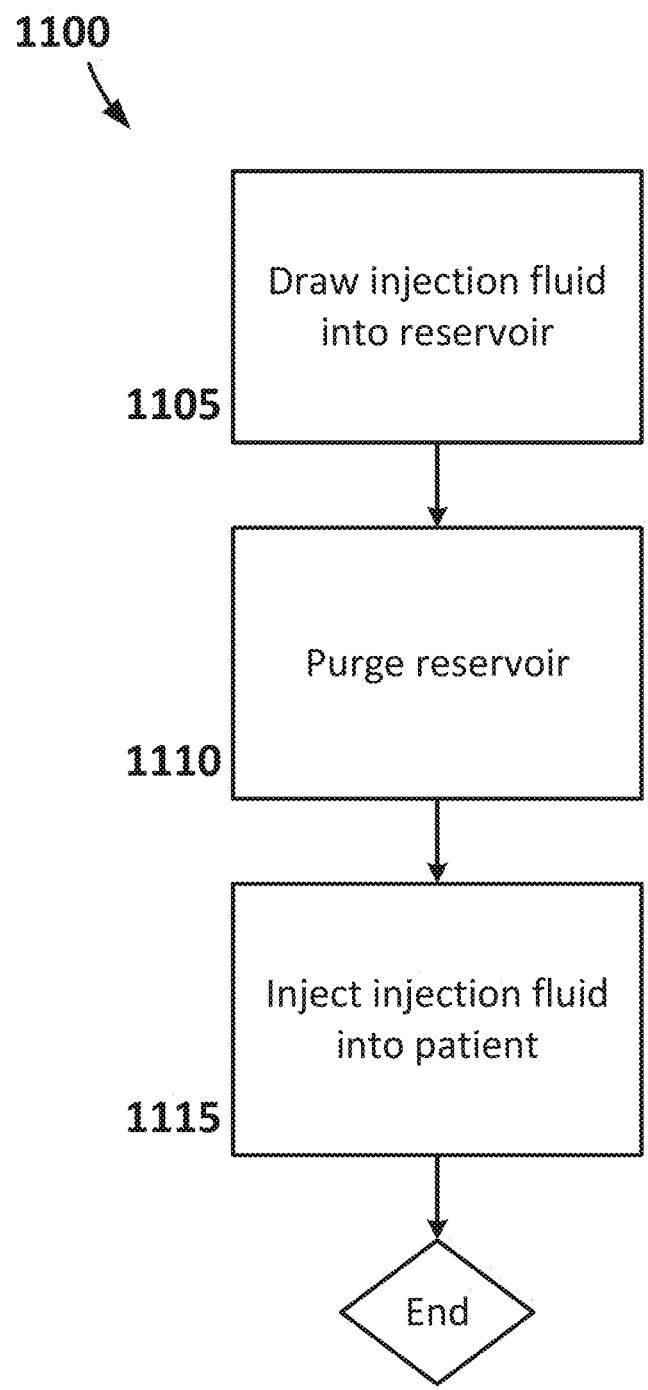
FIG. 10 is a flowchart showing an embodiment of a method of using a fluid injection system.

FIG. 10 is a flowchart illustrating an embodiment of a method 1100 of using a fluid injection system with a valve assembly. The valve assembly in the method 1100 can have one or more (e.g., each) of the features disclosed herein.

At step 1105, the method 1100 includes drawing the injection fluid into reservoir at the fluid injection system. As an example, the operation at step 1105 can be the fill operation described elsewhere herein. In some such examples, drawing injection fluid into the reservoir can include moving the plunger backward (e.g., away from the reservoir fluid inlet) within the reservoir.

At step 1110, the method 1100 includes purging the reservoir at the fluid injection system. As an example, the reservoir can be purged of air as discussed elsewhere herein. In some such examples, purging air from the reservoir can include moving the plunger forward (e.g., toward the reservoir fluid inlet and/or outlet) within the reservoir until no air is present in the reservoir between the plunger and the reservoir inlet and/or outlet. For instance, step 1110 can terminate once only injection fluid is expelled from the reservoir.

At step 1115, the method 1100 includes injecting injection fluid into a patient from the fluid injection system. As an example, injection at step 1115 can be the injection operation described elsewhere herein.

Various examples have been described with reference to certain disclosed embodiments. The embodiments are presented for purposes of illustration and not limitation. One skilled in the art will appreciate that various changes, adaptations, and modifications can be made without departing from the scope of the invention.

What is claimed is:

1. A valve assembly comprising:
a first valve device comprising a first fluid pathway and a first valve member, the first valve member positioned at the first fluid pathway, the first valve member having a first valve member open position that permits fluid flow along the first fluid pathway past the first valve member and a first valve member closed position that prevents fluid flow along the first fluid pathway past the first valve member;
a second valve device comprising a second fluid pathway and a second valve member, the second valve member positioned at the second fluid pathway, the second valve member having a second valve member open position that permits fluid flow along the second fluid pathway past the second valve member and a second valve member closed position that prevents fluid flow along the second fluid pathway past the second valve member; and
a coupling mechanism coupled to each of the first valve member and the second valve member, wherein when the valve assembly is actuated the coupling mechanism is configured to move each of the first valve member from the first valve member open position to the first valve member closed position and the second valve member from the second valve member closed position to the second valve member open position,
wherein the coupling mechanism includes a plurality of actuation sections spaced about a periphery of the coupling mechanism,
wherein the plurality of actuation sections together span a perimeter surface of the coupling mechanism,
wherein each of the plurality of actuation sections has an aperture,
wherein one or both of the first valve fluid pathway and the second valve fluid pathway extend between more than two apertures,
wherein at least one of the first valve fluid pathway and the second valve fluid pathway serves as a fluid inlet, and
wherein at least one of the first valve fluid pathway and the second valve fluid pathway serves as a fluid outlet.

2. The valve assembly of claim 1, wherein when the valve assembly is further actuated the coupling mechanism is further configured to move the second valve member from the second valve member open position to the second valve member closed position.

3. The valve assembly of claim 2, wherein when the valve assembly is further actuated to move the second valve member from the second valve member open position to the second valve member closed position, the coupling mechanism is further configured to maintain the first valve member at the first valve member closed position.

4. The valve assembly of claim 3, wherein the first valve member closed position comprises a first valve member first closed position and a first valve member second closed position that is different from the first valve member first closed position, wherein the coupling mechanism is configured to maintain the first valve member at the first valve member closed position by moving the first valve member from the first valve member first closed position to the first valve member second closed position.

5. The valve assembly of claim 2, wherein, when the second valve member is in the second valve member closed position and the valve assembly is further actuated the coupling mechanism is further configured to move the first valve member from the first valve member closed position to the first valve member open position.

6. The valve assembly of claim 5, wherein when the valve assembly is further actuated to move the first valve member from the first valve member closed position to the first valve member open position, the coupling mechanism is further configured to maintain the second valve member at the second valve member closed position.

7. The valve assembly of claim 6, wherein the second valve member closed position comprises a second valve member first closed position and a second valve member second closed position that is different from the second valve member first closed position, wherein the coupling mechanism is configured to maintain the second valve member at the second valve member closed position by moving the second valve member from the second valve member first closed position to the second valve member second closed position.

8. The valve assembly of claim 1, wherein when the valve assembly is actuated the coupling mechanism is configured to move, at the same time, each of the first valve member from the first valve member open position to the first valve member closed position and the second valve member from the second valve member closed position to the second valve member open position.

9. The valve assembly of claim 1,
wherein the first valve device further comprises a first fluid inlet and a first fluid outlet, wherein the first fluid pathway extends between the first fluid inlet and the first fluid outlet, and wherein the first valve member is positioned at the first fluid pathway between the first fluid inlet and the first fluid outlet, and, wherein the second valve device further comprises a second fluid inlet and a second fluid outlet, wherein the second fluid pathway extends between the second fluid inlet and the second fluid outlet, and wherein the second valve member is positioned at the second fluid pathway between the second fluid inlet and the second fluid outlet.

10. The valve assembly of claim 9,
wherein the first fluid inlet is opposite the first fluid outlet, and the second fluid inlet is opposite the second fluid outlet;
wherein the first fluid pathway is parallel to the second fluid pathway;
wherein the first fluid inlet is adjacent to the second fluid outlet, and the first fluid outlet is adjacent to the second fluid inlet; and
wherein both the first fluid outlet and the second fluid inlet are configured to couple to a fluid injection system reservoir.

11. The valve assembly of claim 1,
wherein the first valve member includes a first valve fluid pathway extending along a first plane through the first valve member, the first valve fluid pathway being in fluid communication with the first fluid pathway when the first valve member is in the first valve member open position, and
wherein the second valve member includes a second valve fluid pathway extending along a second plane through the second valve member, the second valve fluid pathway being in fluid communication with the second fluid pathway when the second valve member is in the second valve member open position, and wherein the first plane is perpendicular to the second plane.

12. The valve assembly of claim 1, wherein the coupling mechanism includes a coupling portion and an actuation portion, wherein the coupling portion is coupled to each of the first valve member and the second valve member, and wherein the actuation portion includes an actuation attachment that is configured to couple to a motive source to receive a motive force to actuate the valve assembly.

13. The valve assembly of claim 12, wherein the actuation attachment comprises a key configured to be complementarily received by a motive source component corresponding to the key.

14. The valve assembly of claim 12, wherein each of the coupling portion and the actuation portion is integrated to form a single-piece coupling mechanism.

15. The valve assembly of claim 12,
wherein the coupling portion of the coupling mechanism further includes a flange, and at least one of the first valve device and the second valve device further includes a retainer configured to receive the flange, and
wherein the coupling mechanism is directly received by each of the first valve device and the second valve device such that the coupling mechanism is retained within the first valve device and the second valve device at the flange.

16. The valve assembly of claim 1, wherein each of the first valve device and the second valve device is integrated to form a single-piece valve device.

17. The valve assembly of claim 1,
wherein the coupling mechanism comprises an elongated shaft,
and wherein the valve assembly is actuated by rotating the coupling mechanism.

18. A fluid injection system comprising:
a reservoir defining an interior reservoir volume, the reservoir including a plunger positioned within the interior reservoir volume;
a drive assembly configured to move the plunger within the interior reservoir volume to draw an injection fluid into the reservoir and to expel the injection fluid from the reservoir; and
a valve assembly fluidly connected to the reservoir, the valve assembly comprising:
a first valve device comprising a first fluid pathway and a first valve member, the first valve member positioned at the first fluid pathway, the first valve member having a first valve member open position that permits fluid flow along the first fluid pathway past the first valve member and a first valve member closed position that prevents fluid flow along the first fluid pathway past the first valve member;
a second valve device comprising a second fluid pathway and a second valve member, the second valve member positioned at the second fluid pathway, the second valve member having a second valve member open position that permits fluid flow along the second fluid pathway past the second valve member and a second valve member closed position that prevents fluid flow along the second fluid pathway past the second valve member; and
a coupling mechanism coupled to each of the first valve member and the second valve member, wherein when the valve assembly is actuated the coupling mechanism is configured to move each of the first valve member from the first valve member open position to the first valve member closed position and the second valve member from the second valve member closed position to the second valve member open position,
wherein the coupling mechanism includes a plurality of actuation sections spaced about a periphery of the coupling mechanism,
wherein the plurality of actuation sections together span a perimeter surface of the coupling mechanism,
wherein each of the plurality of actuation sections has an aperture,
wherein one or both of the first valve fluid pathway and the second valve fluid pathway extend between more than two apertures,
wherein at least one of the first valve fluid pathway and the second valve fluid pathway serves as a fluid inlet, and wherein at least one of the first valve fluid pathway and the second valve fluid pathway serves as a fluid outlet.

19. The fluid injection system of claim 18,
wherein the reservoir further includes a reservoir inlet and a reservoir
outlet; wherein the first valve device is coupled to the reservoir inlet, and
the second valve
device is coupled to the reservoir outlet;
wherein the fluid injection system is configured to perform a fill operation to draw the injection fluid into the reservoir and to perform an inject operation to expel the injection fluid from the reservoir;
wherein when the fluid injection system performs the fill operation, the plunger is moved within the reservoir away from the reservoir outlet by the drive assembly while the first valve member is in the first valve member open position and the second valve member is in the second valve member closed position; and
wherein when the fluid injection system performs the inject operation, the plunger is moved within the reservoir toward the reservoir outlet by the drive assembly while the first valve member is in the first valve member closed position and the second valve member is in the second valve member open position.

20. The fluid injection system of claim 18, wherein the fluid injection system further comprises a motive source coupled to the coupling mechanism of the valve assembly and configured to provide a motive force to actuate the valve assembly;
wherein the coupling mechanism further includes an actuation portion, the actuation portion having an actuation attachment coupled to the motive source and receiving the motive force to actuate the valve assembly; and
wherein, to couple to the motive source, the actuation attachment comprises a key complementarily received by a motive source component corresponding to the key.

* * * * *